United States Patent
Turrini et al.

(10) Patent No.: US 7,320,672 B2
(45) Date of Patent: Jan. 22, 2008

(54) ARTICULATED JOINT FOR A KNEE BRACE WITH ADJUSTABLE ANGULAR EXTENSION

(75) Inventors: Alberto Turrini, Castel d' Azzano (IT); Moreno Ferrigolo, Dossobuono (IT)

(73) Assignee: F.G.P. Srl (IT)

( * ) Notice: Subject to any disclaimer, the term of this patent is extended or adjusted under 35 U.S.C. 154(b) by 271 days.

(21) Appl. No.: 10/547,885

(22) PCT Filed: Feb. 23, 2004

(86) PCT No.: PCT/IT2004/000078

§ 371 (c)(1),
(2), (4) Date: Sep. 2, 2005

(87) PCT Pub. No.: WO2004/078078

PCT Pub. Date: Sep. 16, 2004

(65) Prior Publication Data

US 2006/0173392 A1    Aug. 3, 2006

(30) Foreign Application Priority Data

Mar. 6, 2003   (IT)   .......................... VR2003A0027

(51) Int. Cl.
*A61F 13/00*   (2006.01)
(52) U.S. Cl. .......................................... 602/26; 602/16
(58) Field of Classification Search .................... 602/5, 602/16, 20, 23, 26, 27

See application file for complete search history.

(56) References Cited

U.S. PATENT DOCUMENTS

| 4,791,916 A | 12/1988 | Paez |
| 5,039,247 A | 8/1991 | Young et al. |
| 2004/0049140 A1* | 3/2004 | Doty et al. ................... 602/16 |

FOREIGN PATENT DOCUMENTS

| DE | 36 35 045 A1 | 10/1986 |
| EP | 0 761 186 A2 | 12/1997 |
| EP | 0 615 734 B1 | 2/1998 |

OTHER PUBLICATIONS

International Search Report for International Application No. CT/IT2004/000078 Dated Jun. 29, 2004.

* cited by examiner

*Primary Examiner*—Kim M Lewis
(74) *Attorney, Agent, or Firm*—Greenberg Traurig LLP

(57) ABSTRACT

An articulated joint (10) for a knee brace with controllable angular movement comprises a plate (11) equipped with at least one pair of hinged couplings for respective uprights (12, 13) provided with means of constraint to the femur and to the tibia; the plate (11) presents a shaped central section (15) and at least one housing for a respective extractable insert (25, 26) designed to come into contact against the central section (15) and against at least one longitudinal end of one of the uprights (12, 13).

10 Claims, 3 Drawing Sheets

ARTICULATED JOINT FOR A KNEE BRACE WITH ADJUSTABLE ANGULAR EXTENSION

This application is a national stage filing under 35 U.S.C. 371 of International Application PCT/IT2004/000078, filed on Feb. 23, 2004 which claims priority from Italian Application No: VR2003 A 000027, filed on Mar. 6, 2003. The entire teachings of the referenced Applications are incorporated herein by reference. International Application PCT/IT2004/000078 was published under PCT Article 21(2) in English.

TECHNICAL FIELD

This invention concerns an articulated joint for a knee brace with adjustable angular movement.

More specifically, the invention refers to an articulated joint to control the instability of the posterior cruciate ligament.

The joint is part of a knee brace or support that can be applied during sports activities and post-operative rehabilitation.

The joint can also be applied to control the translation, hyperextension and pathological rotation of the tibia.

This invention can be applied in the medical field with particular reference to manufacturers of prostheses and braces.

BACKGROUND ART

It is known that a subject presenting an injured posterior cruciate ligament, or one which is hyperextended as a result of a previous surgical operation, needs to use a knee brace designed to ensure the function of a hinged restraint between the femur and tibia, supporting stress that would otherwise be damaging for the ligament.

The knee brace usually consists of a rigid frame enclosing the knee in order to ensure an adequate support designed to prevent stress on the ligament when the injured and/or convalescing subject is walking.

The frame comprises means of restraint to the femur and to the tibia close to the knee and a structure connecting these means with a hinged coupling positioned at the level of the knee.

The knee brace frame comprises uprights, positioned laterally with respect to the femur and the tibia, connected by respective articulated joints generally equipped with 4 pivots designed to ensure excellent mobility thanks to the presence of multiple centres of rotation.

To ensure sufficient freedom of movement of the limb, the frame develops almost exclusively at the sides of the knee in order to allow correct reciprocal oscillation between the femur and the tibia.

The means of restraint usually consist of half rings enclosing both the femur and the tibia of the injured person.

The four-pivot articulated joints are used to ensure the hinged connection of the parts of the frame fixed to the femur and the tibia, extending during flexion of the limb and tending to become shorter when the limb is extended.

The risk of movements of the knee brace and of its slipping downwards is thus considerably reduced.

One disadvantage is represented by the fact that such knee braces will improbably allow certain and controllable angular movements, often making it necessary to resort to other ortheses.

It is also known that, depending on the severity of the injury, different people require different degrees of angular movement freedom.

If the possibilities of movement are too limited, the ligaments tend to become even stiffer, while excessive angular movements could further impair the functioning of the already damaged ligaments.

DESCRIPTION OF THE INVENTION

This invention proposes to provide an articulated joint for a knee brace with adjustable angular movement that is able to eliminate or significantly reduce the disadvantages described above.

This invention also proposes to provide an articulated joint for knee braces with which it is possible, with minimum replacement of a few interchangeable parts, to satisfy the requirements of various cases, such as for example for subjects with ligament injuries.

This invention also proposes to provide an articulated joint for knee braces that is easy to produce so as to be advantageous from an economic point of view.

A further aim of this invention is to provide an articulated joint for knee braces with an angular movement that can be controlled, is safe and reliable in order not to cause damage to the injured subject using it.

This is achieved by means of an articulated joint for knee braces with a controllable angular movement with the features described in the main claim.

The dependent claims describe advantageous embodiments of the invention.

The articulated joint for knee braces with controllable angular movement according to this invention comprises a plate equipped with at least one pair of hinged couplings for respective uprights provided with means of constraint to the femur and the tibia, this plate presenting a shaped central section and at least one housing for a respective extractable insert, designed to come into contact with the central section and with at least one longitudinal end of an upright.

According to the invention the articulated joint comprises means of temporary restraint for the inserts in order to keep them firmly fixed to the plate.

The shaped section can be extracted and therefore replaced with another differently shaped section.

The shape of the section and the inserts is such as to limit the reciprocal angular movement between the upright constrained to the femur and the upright constrained to the tibia.

This shape is differently represented on the inserts in order to obtain different angular movements in relation to the various inserts used.

The articulated joint has concealed housings for the inserts, consisting of slots in the thickness of the plate.

The base of the plate, at the level of each slot, presents an opening designed to make the housing of the respective insert visible.

According to an advantageous embodiment of the invention, the means of temporary restraint of the inserts to the plate consist of screws which can be screwed into the base surface through easily accessible holes.

The articulated joint is made from lightweight metal alloy or high-resistance composite plastic material, the surface resting against the limb being, in any case, made from an allergic material.

DESCRIPTION OF THE DRAWINGS other features and advantages of the invention will become evident on reading the description below of one embodiment of the invention, given as a non-binding example, with the help of the attached drawings in which.

DESCRIPTION OF ONE EMBODIMENT

Figure 1:
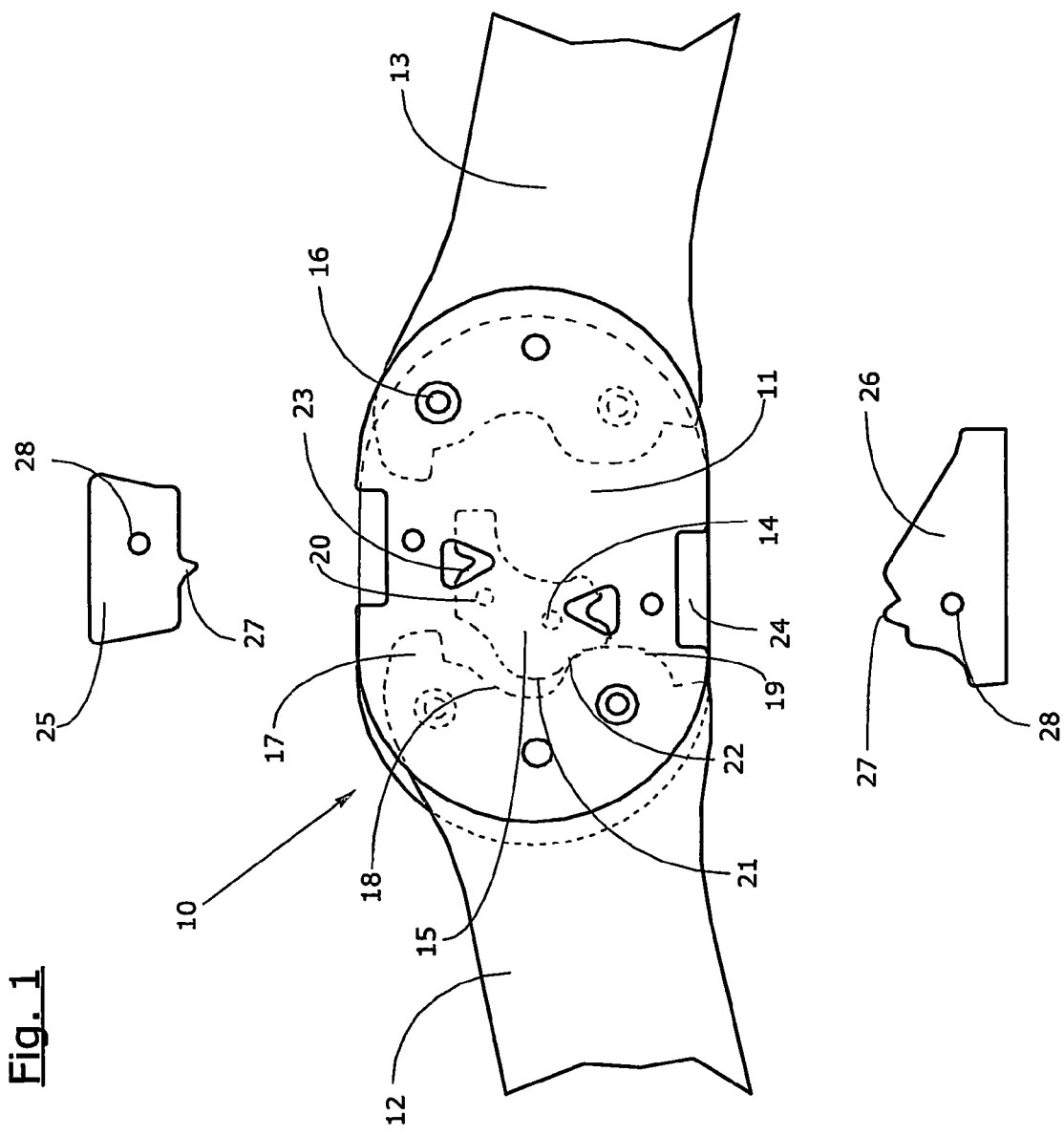
FIG. 1 shows an elevated side cross-section view of an articulated joint according to the invention, with the inserts removed.

With reference first of all to FIG. 1, the reference number 10 indicates in general an articulated joint, in the case in question an articulated joint 10 for a knee brace with controllable angular movement.

The articulated joint 10 according to the invention comprises a plate 11 which is internally hollow in order to accommodate the longitudinal ends of a femoral upright 12 and a tibial upright 13.

A shaped section 15 is fixed to the central inner portion of the plate, for example by means of snap-in pins 14.

The plate 11 is equipped with two hinged couplings 16 for each upright 12, 13 which are thus free to swivel with respect to the articulated joint.

According to a particularly advantageous embodiment of the invention, each upright 12, 13 has a shaped longitudinal end with a stop tooth 17, at least one concave portion 18 and at least one convex portion 19.

The section 15 has central holes 20, designed to accommodate the respective pins 14 of the plate 11, and a perimeter shaped with convex curves 21 and concave curves 22 facing the longitudinal end of one of the uprights 12 or 13. The perimeter of the shaped section 15 also has notches 23 on two opposite sides.

Figure 2:
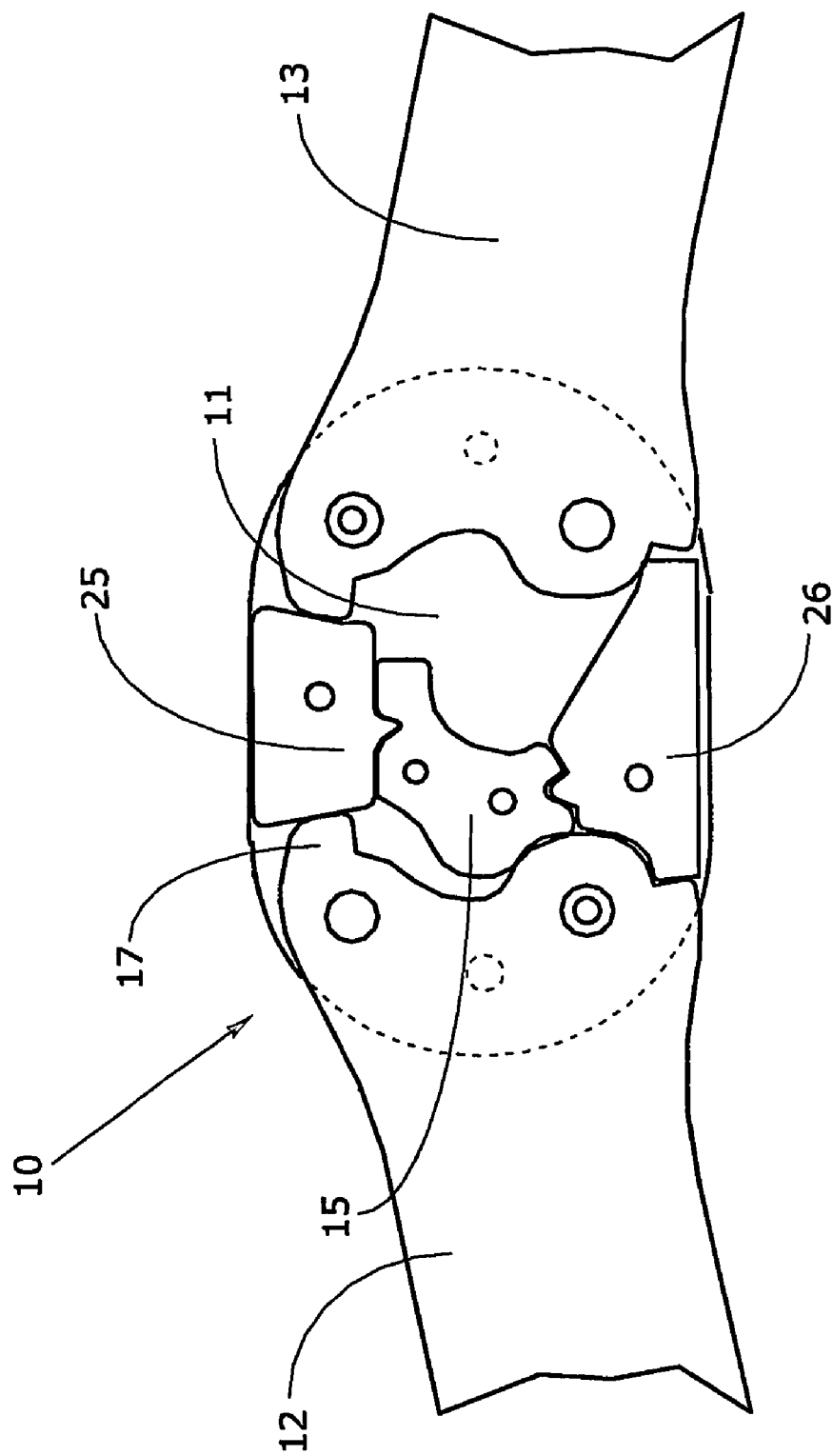
FIG. 2 shows a view similar to that in FIG. 1 but with the inserts in their housings and the plate of the joint open.

As can be seen by examining FIGS. 1 and 2, the articulated joint 10 according to the invention has transverse slots 24 designed to accommodate inserts 25, 26 which can be temporarily blocked inside the plate 11 and coming into contact against both the longitudinal ends of the uprights 12, 13, and against the shaped section 15.

Each insert 25, 26 presents a blade-like configuration with a profile presenting a tooth 27 which can be accommodated in the respective notch 23 in the section 15.

According to a particular embodiment of the invention, the insert 25 can be trapezoidal in shape, while the insert 26 can, for example, have a polygonal shape.

Each insert 25, 26 has a central hole 28 designed to accommodate a screw (not shown in the drawings) to fix the insert 25, 26 to the shaped section 15.

Figure 3:
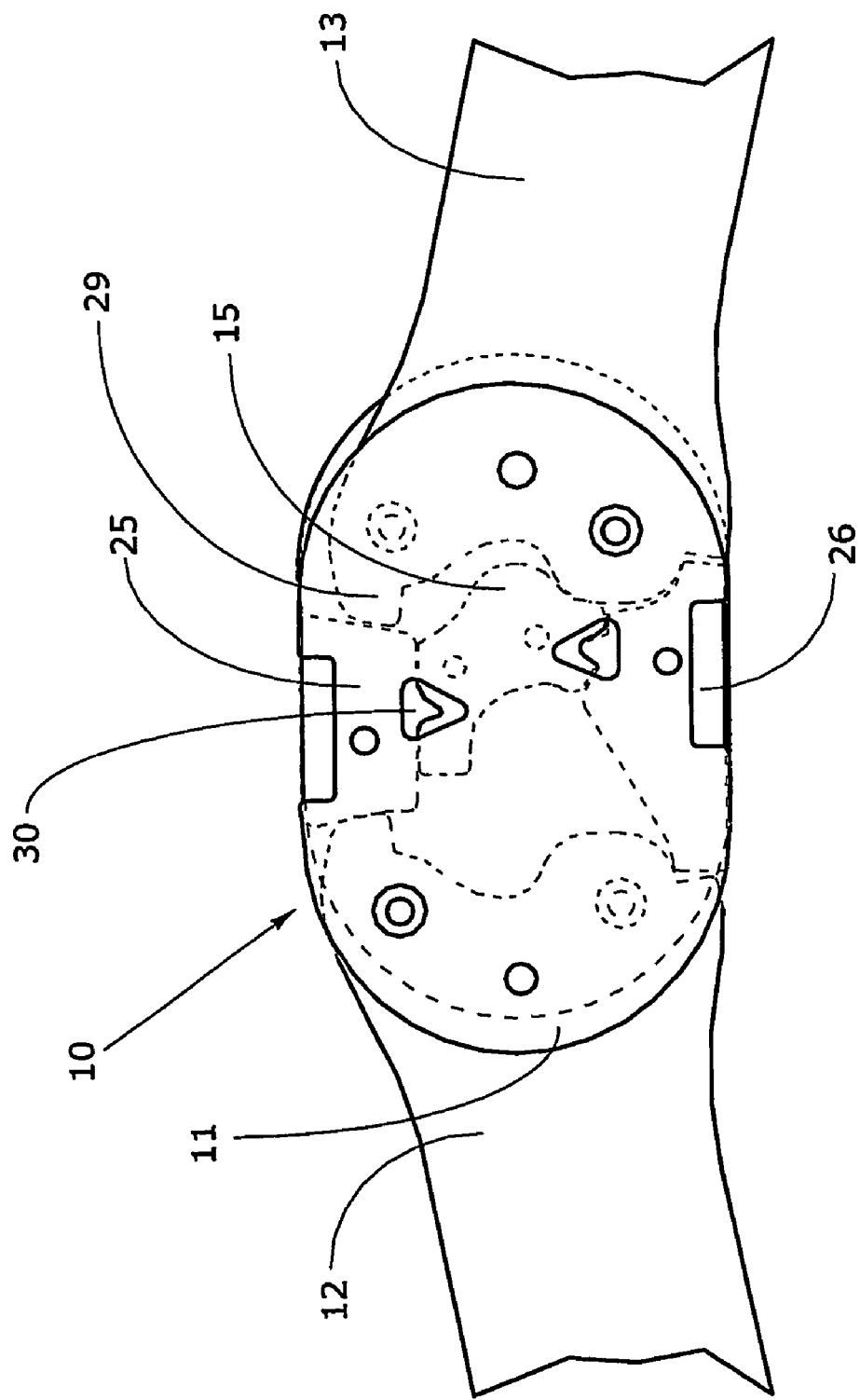
FIG. 3 is an elevated front view of the joint.

With reference to FIG. 3, it can be seen that at least one outer base surface 29 of the section 15 has openings 30 corresponding to a respective insert 25 or 26.

The openings 30 are advantageously designed to visualise the presence of the insert 25 or 26 in the respective housing inside the joint 10.

The presence of the teeth 27 ensures a correct contact of the inserts 25, 26 against the shaped section 15 ensuring a precise positioning with respect to the concave 18 and convex portions 19 of the longitudinal ends of each upright 12, 13.

These concave 18 and convex portions 19 rest against the respective curvatures 21 and 22 of the shaped section 15 according to this particularly advantageous embodiment of the invention, while the stop tooth 17 ensures the end of stroke of the angular movement of the upright 12 or 13 with respect to the articulated joint 10.

The shaped section 15 and the inserts 25, 26 are modular in nature and can thus be replaced by other respective components which are similar but have a differently shaped perimeter edge.

It is thus possible to obtain different angular movements of the uprights 12, 13 with respect to the plate 11, adapting the use of the articulated joint 10 to the specific requirements of the user.

The base surface 29 of the plate 11, which when fitted is facing the limb of the injured subject, is advantageously made from an allergic material to limit the risks of allergic phenomena and/or reddening of the skin in contact with the joint.

The articulated joint 10 can be made from lightweight metal alloy or high-resistance composite plastic material.

The invention is described above with reference to a preferred embodiment.

The invention is nevertheless susceptible to numerous variations which are within the framework of mechanical equivalents.

The invention claimed is:

1. An articulated joint for a knee brace with controllable angular movement, comprising a plate equipped with at least one pair of hinged couplings for respective uprights provided with means of constraint to the femur and to the tibia, whereby said plate has a shaped central section and at least one housing for a respective extractable insert designed to come into contact against the central section and against at least one longitudinal end of one of the uprights, said joint further comprising means of temporary restraint of the inserts to the plate, wherein the shaped section and the inserts are interchangeable with other similar respective components with a different perimeter configuration.

2. The articulated joint of claim 1, wherein the longitudinal end of each upright comprises a stop tooth, at least one concave portion and at least one convex portion.

3. The articulated joint of claim 1, wherein the shaped section has a perimeter with convex curvatures and concave curvatures facing the longitudinal end of one of the uprights.

4. The articulated joint of claim 1, wherein the perimeter of the shaped section shows notches on two opposite sides.

5. The articulated joint of claim 1, wherein each insert has a blade-like configuration with its edge having a tooth which can be accommodated inside the respective notch in the shaped section.

6. The articulated joint of claim 1, wherein the means of temporary restraint of the inserts to the plate consist of screws.

7. The articulated joint of claim 1, wherein at least one outer base surface of the shaped section presents openings at the connection of the respective insert with a notch in the shaped section.

8. The articulated joint of claim 1, wherein the housing of the insert is concealed.

9. The articulated joint of claim 1, wherein the articulated joint is made from a lightweight metal alloy and/or high-resistance composite plastic material.

10. A knee brace or support comprising at least one articulated joint according to claim 1.

* * * * *